US006498029B2

(12) United States Patent
Keller, Jr. et al.

(10) Patent No.: US 6,498,029 B2
(45) Date of Patent: Dec. 24, 2002

(54) **PENTOSE FERMENTATION OF NORMALLY TOXIC LIGNOCELLULOSE PREHYDROLYSATE WITH STRAIN OF *PICHIA STIPITIS* YEAST USING AIR**

(75) Inventors: Fred A. Keller, Jr., Lakewood, CO (US); Quang A. Nguyen, Golden, CO (US)

(73) Assignee: Midwest Research Institute, Kansas City, MO (US)

( * ) Notice: Subject to any disclaimer, the term of this patent is extended or adjusted under 35 U.S.C. 154(b) by 0 days.

(21) Appl. No.: 09/886,581

(22) Filed: Jun. 21, 2001

(65) Prior Publication Data

US 2001/0036659 A1 Nov. 1, 2001

Related U.S. Application Data

(63) Continuation-in-part of application No. 09/442,431, filed on Nov. 17, 1999.

(51) Int. Cl.[7] .................................................. C12N 1/16
(52) U.S. Cl. ................................ 435/255.5; 435/255.1; 435/938
(58) Field of Search ........................... 435/255.5, 255.1, 435/938

(56) References Cited

U.S. PATENT DOCUMENTS 4,701,414 A * 10/1987 Van Dijken et al. ........ 435/163

OTHER PUBLICATIONS

Amartey et al. Biotechnology Letters, Feb. 1994. vol. 16, No. 2, pp. 211–214.*
Keller et al. Applied Biochemistry and Biotechnology. 1988. vol. 70–72, pp. 137–148.*

* cited by examiner

*Primary Examiner*—Irene Marx
*Assistant Examiner*—Vera Afremova
(74) *Attorney, Agent, or Firm*—Paul J. White

(57) ABSTRACT

Strains of the yeast *Pichia stipitis* NPw9 (ATCC PTA-3717) useful for the production of ethanol using oxygen for growth while fermenting normally toxic lignocellulosic prehydrolysates.

20 Claims, No Drawings

PENTOSE FERMENTATION OF NORMALLY TOXIC LIGNOCELLULOSE PREHYDROLYSATE WITH STRAIN OF PICHIA STIPITIS YEAST USING AIR

The invention is a continuation-in-part of U.S. patent application Ser. No. 09/442,431, filed Nov. 17, 1999, and relates to a new strain of the yeast *Pichia stipitis* strain NPw9 having accession ATCC No. PTA-3717, deposited at ATCC, 10801 University Boulevard, Manassas, VA 20110 and also known as *Yamadazyma stipitis* and a process for preparation of the new strain of the yeast *Pichia stipitis* capable of producing ethanol from usually toxic levels of prehydrolysate hexose as well as pentose sugars and is also capable of producing more cell mass, as a result of controlling aeration levels, than is possible for typical or wild-type yeast fermentation of sugars. These normally toxic levels of prehydrolysate sugars significantly reduce contamination by competing organisms and therefore reduce the need and costs for sterilization of the prehydrolysate prior to fermentation.

CONTRACTUAL ORIGIN OF THE INVENTION

The United States Government has rights in this invention pursuant to Contract No. DE-AC36-99G010337 between the United States Department of Energy and the National Renewable Energy Laboratory, a Division of the Midwest Research Institute.

FIELD OF THE INVENTION

BACKGROUND OF THE INVENTION

Effort to produce renewable alternative sources of transportation fuels from biomass have resulted in considerable progress in the conversion of hardwood and agricultural waste into ethanol. Added yields could be expected if the pentosan hemicellulose (five carbon sugar polymers), in addition to hexoses and cellulose, could be effectively fermented to ethanol.

Softwood Prehydrolysates

However, except for sulfite waste liquor, reports of the conversion of softwood materials to ethanol have been limited. Furthermore, the hemicellulose for most softwoods studied is primarily hexosan, composed mainly of mannose with smaller amounts of glucose and galactose, as well as some pentoses. Traditional *Saccharomyces cerevisiae* yeast cultures ferment these hexoses very well, and would be expected to produce high ethanol yields if they could tolerate low concentrations of countless toxins present in dilute acid prehydrolysates generated from softwoods. Typically, these prehydrolysates are generated to produce monomeric sugars from carbohydrate polymers and/or to improve enzymatic digestibility of cellulose in forest waste, municipal solid waste (MSW), or agricultural waste. This biomass is usually converted into a prehydrolysate slurry by soaking the biomass in dilute acid (0.1% to 4%), draining, and then steaming it at about 170° to 215° C. for 30 to 360 seconds.

Prehydrolysates from softwoods are believed to be more toxic than those from agricultural wastes or hardwood biomass sources, because softwoods usually contain more extractives and often more bark than do hardwoods. Consequently, if a process is found to ferment softwood prehydrolysate, fermentation of other prehydrolysates should directly follow. Potential toxic substances include biomass components themselves, particularly extractives such as terpenes, aldehydes, and polyhydroxy aromatics. Other sources of toxins are prehydrolysis products and degradation products including acetic acid from acetylated sugars, furfural, and hydroxy-methyl furfural, the initial degradation products from pentose and hexose sugars, respectively, and oligomers formed by reaction of the furfurals with sugars. Degradation of coniferous lignin yields complex guaiacyl propyl units. Corrosion products from equipment also can be toxic, or the metallic ions can behave as catalysts to produce additional products.

Fortunately most of the toxins in well-prepared prehydrolysate are present at less than one g/L, and only a very few, such as furfural, are present at a few g/L. However, over time, yeast can adapt themselves to tolerate many of these substances in the presence of glucose sugar—but the adaptation in the presence of these toxins prevent or greatly reduce growth and ethanol production.

Yeast Bioreactions and Fermentation

It is generally well known that *Saccharomyces cerevisiae* yeast aerobically oxidizes low concentrations of sugars in aqueous solutions to produce yeast cell mass, carbon dioxide and water, in accordance with the following equation:

1) 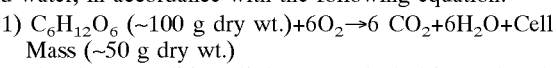
   Mass (~50 g dry wt.)

Under these conditions little or no alcohol is produced. This is how bakers yeast is produced. However, at higher concentrations of sugar, even in the presence of much air, the sugar shuts down the oxidative metabolism of the yeast (the Crabtree effect), and the yeast then ferments the sugars to ethyl alcohol (ethanol), one-third the amount of carbon dioxide, much less cell mass, and no measurable amount of water in accordance with the equation:

2) 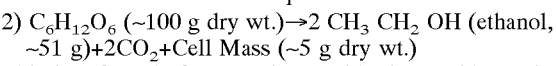
   ~51 g)+2CO$_2$+Cell Mass (~5 g dry wt.)

This is a forced "fermentation," with air or without air, because of the Crabtree effect. In the correct sense, fermentation is a term for conversion of sugar to ethanol. Unfortunately, this term has been loosely used for any type of microbial metabolism, even bio-oxidation, by any organism. The loose use of the term fermentation has lead to considerable confusion.

For example, in much of the prior art, even the oxidative conversion of sugars primarily to bakers yeast cell mass is referred to as fermentation.

Prior Art

U.S. Pat. No. 5,693,526 disclose novel strains of yeast *S. cerevisiae* for ethanol production using a number of different hybridization methods for obtaining improved flocculation, improved growth on 40% to 50% molasses (high sugar concentration), and growing in the presence of 7% to 12% ethanol. In this reference, there is no disclosure of hydrolysate, little or nothing on aeration, and little or nothing on low nutrient or on simultaneous aeration, low nutrient, and hydrolysate adaptation.

A process for making yeast tolerant to high pressure in which yeast are transformed with foreign DNA to encode for two enzymes, superoxide dismutase and catalase is disclosed in U.S. Pat. No. 5,674,721. This patent tests the transformed cells to show that they are twice as heat tolerant as the original yeast cells by heating them in the air at about 50° C. The patent does not disclose hydrolysate, evidences little or no discussion on aeration during growth or fermentation, evidences no appreciation for low nutrient or simultaneous aeration, and hydrolysate adaptation.

U.S. Pat. No. 4,567,145 disclose used respiration deficient yeast, and makes no reference to respiration enhanced yeast. This patent does not claim tolerance to hydrolysate nor adaptation to low nutrients. Further, there is no reference in this patent to simultaneous aeration, low nutrient, and hydrolysate adaptation.

Processes for screening aerobic yeast produced from hybridization or mutation using two tests for bread-making which do not use gas-release measurement, such as more growth on maltose, or more growth on sour (acid) dough are disclosed in U.S. Pat. Nos. 4,396,632; 4,318,929 and 4,318,930. These patents generate their yeast by hybridization and mutation, and test these yeast to determine whether they have improved in their performance. These patents do not generate their new strains naturally by simultaneous acclamation under severe constraints over time. Further, the processes in these patents are fully aerobic yeast metabolism, for making bakers yeast. These processes are not fermentation producing ethanol.

U.S. Pat. No. 4,477,569 disclose pentose fermentation by yeast *Pachysolen tannophilus* (not *S. cerevisiae*) with air in the first stage and with improved yield with recycle. The pathway in this process is different and this pathway is not known to exist in *S. cerevisiae*. This patent uses a very rich, very expensive medium including yeast nitrogen base, yeast extract, and casamino acids along with its sugars. Further, this patent states that air is not needed with cell recycling and also uses the mutagen, ethyl methanesulfonate. The patent does not use hydrolysate and does not adapt its cells to tolerate the toxic hydrolysate at very low, inexpensive nutrients simultaneously.

An aerobic fermentation is disclosed for production of high-density yeast cell mass, but not ethanol, in U.S. Pat. No. 4,414,329. The high cell densities are produced in a continuous stirred tank bioreactor by continually feeding mineral salts with the carbon source feed, to eventually achieve cells with high mineral content.

U.S. Pat. No. 3,384,553 disclose a method for aerobic fermentation in which the dissolved oxygen concentration in liquid medium for cultivation of microbes is controlled by the rate of addition of medium to the culture. This patent does not disclose the actual production of ethanol by true fermentation:

"Yeast Adaptation on Softwood Hydrolysate", in Applied Biochemistry and Biotechnology 70–72, 137–148 (1998) disclose that the highest equivalent total solids (ETS) fermentable hydrolysate concentration is up to 17%, at which concentration we learned that the culture stalled out. In the publication, the concentration of the culture was dying off faster than it was growing, and anything higher than 17% could not be sustained at that time. Therefore, there was a need to diagnose the reason for the stalling out and to over come it by forcing the yeast mitochondria to function.

Accordingly, a need existed to obtain yeast functioning mitochondria at high sugar level concentrations, which normally repressed yeast mitochondria.

There is also a need in the art of utilizing yeast to ferment ethanol from sugars to provide new strains of yeast able to use oxygen for growth while fermenting "Crabtree negative," normally toxic concentrations of hexose containing wood prehydrolysates to ethanol.

There is further need in the art of fermenting sugars to ethanol from toxic levels of prehydrolysates sugars, to also produce more cell mass, that is not possible in typical "Crabtree positive" yeast fermentation of sugars.

A yet further need in the art of producing ethanol from fermentation of sugars in the normally toxic softwood prehydrolysate environment is to provide new strains of yeast that are not contaminated by any wild organism.

SUMMARY OF THE INVENTION

One object of the present invention is to provide new yeast strains of *Pichia stipitis* that are able to use oxygen for growth while fermenting normally toxic concentrations of xylose containing wood prehydrolysates to ethanol.

Another object of the present invention is to provide new yeast strains of *Pichia stipitis* capable of not only producing ethanol from toxic levels of prehydrolysate sugars, but also producing more cell mass.

A further object of the present invention is to provide new strains of the yeast *Pichia stipitis* capable of producing ethanol from toxic levels of prehydrolysate sugars, while producing more cell mass, by controlling aeration and nitrogen-source levels.

A still further object of the present invention is to provide new strains of the yeast *Pichia stipitis* able to use oxygen for growth while fermenting normally toxic concentrations of xylose as well as hexose containing wood prehydrolysates to ethanol, wherein the new yeast strains have the ability of maintaining a growth rate in excess of the death rate in toxic fermentation broth.

A yet further object of the present invention is to provide a new yeast strain of *Pichia stipitis*, designated NPw9 that is cultured in normally toxic wood prehydrolysates, that has never been contaminated by any wild organism.

A still further object of the invention is to provide a new yeast strain of *Pichia stipitis* Npw9 capable of fermenting equivalent total solids (ETS) hydrolysates at concentrations in excess of 17% without incurring the culture stall-out experienced at this level of equivalent total solids, by achieving functioning mitochondria at higher than 17% hydrolysate concentrations by reducing the nutrient concentration, while increasing aeration, and simultaneously increasing the hydrolysate concentration.

A further object of the present invention is to provide new yeast strains of *Pichia stipitis* NPw9, capable of using oxygen for growth while fermenting xylose in wood prehydrolysates to ethanol that are not only cost-effective, reducing the need for sterilization, but very robust and ideal for large-scale commercial production.

A further object yet still of the present invention is to provide a new yeast strain of *Pichia stipitis* of designation NPw9 that is cultured in normally toxic wood prehydrolysates, that has never been contaminated by any wild organism.

DETAILED DESCRIPTION OF THE INVENTION

The choice of *Saccharomyces cerevisiae* yeasts in U.S. application Ser. No. 09/442,431 filed Nov. 17, 1999, is well suited to fermentation of softwood prehydrolysates to ethanol in high yield because softwood prehydrolysates contain predominately hexose sugars, and these yeast ferment all three six-carbon hexoses found in softwood prehydrolysates.

However, as noted in the first paragraph of the Background of the Invention of Ser. No. 09/442,431, which discusses hardwood and agricultural wastes that contain pentosan hemicellulose (five-carbon sugar polymers), "Added yields could be expected if the pentosan hemicellulose could be effectively fermented to ethanol." The literature indicated that a few species of yeast ferment five-carbon sugars well but used expensive nutrients, and could not tolerate significant concentrations of toxic compounds in pentosan-containing prehydrolysates[1,2,3] without some type of costly detoxification.

Consequently, after developing yeast that now can produce high ethanol yields from three hexoses in toxic levels of softwood prehydrolysate, at low nutrient concentrations, and

[1] A. Taivola et al, Alcoholic fermentation of D-xylose by yeasts, Applied and environmental microbiology, 47, 1221-1223, (1984). [2] M. J. Beck, Factors affecting efficiency of biomass fermentation to ethanol, Biotechnology and Bioengineering Symp. No. 17, 717-627, (1986). [3] J. C. du Preez et al., The fermentation of hexose and pentose sugars by Candida shehatea and *Pichia stipitis*, Applied Microbiology and Biotechnology, 23, 228-233, (1986). without costly prehydrolysate detoxification, our attention turned to species of aerobic yeasts that can ferment five-carbon sugars, particularly xylose. Xylose is the predominant five-carbon sugar in pentosan hemicellulose.

Applying the process of the invention to the yeast, which was found to be the best at fermenting xylose in screening cultures containing low concentrations of softwood and hardwood prehydrolysates, we screened two Candida species, shehatae, and acidothermophilum; *Schizosaccharomyces pombe; Pachysolen tannophilus*; and *Pichia stipitis*.

The new genus and species of five-carbon sugar-fermenting yeasts that performed best to date, is *Pichia stipitis*, also known as *Yamadazyma stipitis*, which is the imperfect yeast stage of *Candida shehatae*[4]

The fermentation stoichiometry appears to be in accord with the following equation:

$$3C_5H_{10}O_5 \text{ (~100 g dry xylose)} \rightarrow 5CH_3CH_2OH \text{ (~51 g ethanol)} + 5CO_2 + \text{Cell Mass (~5 g dry cell wt.)}$$

EXAMPLE (C5 Sugar Fermentation)

The new *Pichia stipitis* yeast strain, NPw9, was prepared from native *Pichia stipitis* yeast, (NRRL#Y-11544) which is in the public domain, using a special aerobic adaptation and growth process using as fermentation medium the normally toxic, acid prehydrolysate slurries from agricultural and wood wastes. The native *Pichia stipitis* was obtained from the Northern Region Research Lab (NRRL), Agricultural Research Service, USDA, 1815 N. University St., Peoria, Ill. 61604.

Phenotypic characteristics of the new yeast are observable characteristics of yeast produced from the interaction of the environment on the yeast genotype.

The yeast *Pichia stipitis* strains was adapted over time to grow on usually toxic, acidic (pH 5.0 or lower) prehydrolysate slurry prepared from hardwood, or softwood. One of the first woods used was yellow poplar.

Prehydrolysate, prepared from this poplar sawdust, was about 20% (w/w) total solids. The yeast strain derived from *Pichia stipitis*, NRRL #Y-11544 is called NPw9. The prehydrolysate liquor filtrate, or pressate, free from insoluble solids, is prepared from mixed softwood. It is described as 37% (w/w) equivalent total solids (ETS). It is diluted initially to 6% ETS. The diluent is water and a sugar syrup concentrate such that the initial 6% ETS culture

[4] 4 ATCC Catalog of Yeasts, 18th Edition, 12301 Parklawn Drive, Rockville, Md. 20852-1776, *Pichia stipitis*, p.49, *Yamadazyma stipitis*, 99, (1990). broth contains approximately the same total sugar concentration as the target prehydrolysate.

The target prehydrolysate sugar concentration is the highest total sugar concentration obtained after extracting the prehydrolysate sugar syrup from its solids, typically 24% ETS, using the minimum amount of diluent, usually water.

The 37% ETS prehydrolysate liquor filtrate (or pressate) is used for preparing yeast cultures, rather than using the whole slurry. The cultures were adapted to grow on 24% ETS prehydrolysate or higher concentrations, by gradually increasing the prehydrolysate concentration, and keeping the total sugar concentration constant while increasing aeration and decreasing medium nutrients and nutrient concentrations, as described in the next section.

The adaptation procedure, in other respects, is similar to that used for obtaining Nx7 and Nu6 strains of *Saccharomyces cerevisiae* yeast, after those cultures stalled out at prehydrolysate concentrations higher than 17%.

1) prehydrolysates used are prepared from substrates, such as agricultural wastes, grain milling wastes, poplar sawdust and whole-tree-softwood blends (this material is whole tree, mixed forest thinnings, including bark and twigs);
2) the concentrations of these prehydrolysates in the cultures are gradually increased.
3) for *Pichia stipitis* cultures, stalling out at ~17% prehydrolysate concentrations was avoided by applying what we learned with Nx7 and Nu6. We encouraged functioning mitochondria at high sugar concentrations by reducing the nutrient concentration, while:
4) we increased aeration, and simultaneously increased the prehydrolysate concentration.

In a similar fashion to the Nx7 yeast, in the presence of sugar, air, low nutrient-concentration, and 24% prehydrolysate concentration, the NPw9 Pichia yeast produced good cell growth (>0.4 g/L) with high viability (>90%).

The essence of the invention resides in:
1) gradually increasing the culture ETS concentrations, while:
2) maintaining the cell population at ~$10^8$ cells/mL and at least 90% viability, as 30 determined by Wofford staining.[5]

[5] Mc. Donald, V. R. I Food Science 28 (#1), 135 (1963).

3) providing aeration (~0.001 to >0.7 mM $O_2$/L. min) during the adaptation period;
4) simultaneously decreasing the nutrient concentration toward a target level. (The preferred target is ~0.5% (w/v) clarified corn steep liquor (cCSL), and 0.5% (w/v) ammonium sulfate, or the equivalents thereof). Clarified CSL prehydrolysate may be used at times to facilitate microscopic culture examination.

It was found that decreasing nutrients in the presence of air forced the yeast cells to maintain functioning mitochondria that enable them to synthesize nutrients in order to survive, while gradually increasing the prehydrolysate concentration. A visible indication noted at that time is that truly growing cells will give the black pressate at a lighter, buff hue within 16 to 36 hours, noticeable when the culture is shaken. Otherwise the population viability declines.

Once the yeast were thereby modified, the air supply rate may be greatly reduced to <0.007 mM $O_2$/L. min. Keeping significant levels of sugars, especially dextrose, whenever cultures were grown on toxic pressate, during this time of adaptation further reduced death rate, while obliging mitochrondrial activity. Dextrose was monitored by YSI and dextrose or prehydrolysate or sugar concentrate was added if the dextrose concentration dropped below 10 g/L.

During the adaptation process, the number of cell generations were maximized and all generated cells were used by splitting, and transferring culture progeny into additional cultures usually of gradually increasing prehydrolysate concentrations. Also, the yeast adaptation was conducted while they had active mitochondria. This was accomplished in shake-flasks where an oxygen absorption rate of approximately 0.001 to $\geq$0.7 mM $O_2$/L. min. was provided. The oxygen not only allows the yeast to synthesize several nutrients (that did not need to be added) but also apparently enhances and directs evolving mitochrondrial and ribosomal modifications during this adaptation.

As part of the yeast adaptation effort, concentrations of yeast extract and peptone were reduced and then replaced by inexpensive cCSL and ammonium sulfate with aeration of $\geq$0.001 mM $_2$/L.min, while maintaining sustained growth-rates in excess of the death-rate, as confirmed by viability checks.

As an example, 1% (w/w) yeast extract was replaced by clarified corn steep liquor. Two percent (w/w) peptone was replaced with 0.255 to 1.5% (w/v) ammonium sulfate. At 5% (w/v) hexose sugars, or less, the ammonium sulfate gradually is reduced further to ~0.5%.

These new yeast mutants represent new compositions of matter.

Without detoxification of softwood or hardwood or agricultural residue prehydrolysates, using the *Pichia stipitis* NPw9 strain, 60% to 80% of theoretical ethanol yields are obtained in 47 hours from at least four sugars with excess aeration and nitrogen source (1.5% ammonium sulfate). Typically, fermentation of *Pichia stipitis* NPw9 with excess aeration on 55.6% (v/v) prehydrolysate (equivalent to 20% ETS), containing 26.21 g/L glucose (G), 13.16 g/L xylose (X), 7.03 g/L galactose (Gal), 3.60 g/L arabinose (A), and 24.36 g/L mannose (M), produced 54.14 g ethanol/L in 47 hours.

At this time, the average theoretical ethanol yield from the four sugars is over 75%; and ~100%, 17.9%, 33.3% and 97.7% ethanol yield from each sugar, G, X, Gal and M, respectively. Ethanol yields from xylose and galactose are increased to over 90%, later in the fermentation, by reducing aeration. Further adaptation reduces the fermentation time needed to obtain complete fermentation and high-yield. Similarly, cell mass yields from ~10% (w/w) of the hexose carbon used, to less than 2%, respectively, have been generated by controlling nitrogen source concentration and/or using micro-aerophillic levels of oxygen.

Controlling oxygen absorption rates can be used in addition to controlling nitrogen source, to regulate fermentative cell yield at low nutrient level, thereby allowing the new yeast strain to remain viable in toxic fermentation broths and out-compete other fermentative organisms.

As a result of this ability of the new yeast, and the fact that it is not necessary to detoxify the prehydrolysate, the chance of contamination by unwanted microorganisms is substantially reduced.

NOTE: Some strains of *P. Stipitis* have the desirable characteristic of fermenting arabinose. It is not clear at this time if NPw9, or its parent, NRRL #y-11544, ferments arabinose or not. Otherwise, a new parent that ferments arabinose is selected and the adaptation is repeated, if the feedstock contains significant concentrations of arabinose.

We claim:

1. A biologically pure culture of *Pichia stipitis* strain NPw9 having ATCC accession No. PTA-3717 useful for production of ethanol using oxygen for growth while fermenting toxic lignocellulosic prehydrolysates in excess of 17% equivalent total solids and/or municipal solid waste (MSW) without detoxifying said lignocellulosic prehydrolysates.

2. A process for the preparation of *Pichia stipitis* strain NPw9 having ATCC accession No. PTA-3717 comprising:
   a) growing a culture of *Pichia stipitis* yeast on toxic prehydrolysates of agricultural residues, grain processing intermediates and residues, softwoods, hardwoods or mixtures thereof;
   b) maximizing the number of cell generations and using all generated cells by splitting and transferring culture progeny into additional cultures while said yeast have active mitochondria by gradually increasing prehydrolysate concentration while increasing aeration and reducing nutrient concentration in an amount sufficient to obligate yeast dependency on oxygen at an oxygen absorption rate of 0.001 to $\leq 0.7$ mM of $O_2$ per liter of culture per minute;
   c) gradually substituting for yeast extract a lesser amount of corn-steep liquor;
   d) replacing a nitrogen source of peptone with a lesser amount of ammonium sulfate, or an inexpensive nitrogen source; and
   e) collecting cells of *Pichia stipitis* strain NPw9 having accession No. PTA-3717.

3. The process of claim 2 wherein said toxic prehydrolysate is debarked softwood Douglas fir.

4. The process of claim 2 wherein said toxic prehydrolysate is a blend of whole tree softwoods of White Fir and Ponderosa Pine.

5. The process of claim 2, wherein said toxic prehydrolysate is a blend of mixed softwood or hardwood, or a blend of mixed woods.

6. The process of claim 2, wherein said prehydrolysate is derived from agricultural residues grain processing intermediates and residues, and/or MSW, or blends thereof.

7. The process of claims 3, 4, 5, or 6 wherein said toxic prehydrolysate is in the form of a slurry.

8. The process of claims 4, 5, or 6 wherein said toxic prehydrolysate is in the form of a filtrate.

9. The process of claim 8 wherein said toxic prehydrolysate has a pH of about 6.0 to about 3.0.

10. A process for preparation of *Pichia stipitis* strain NPw9 having ATCC accession No. PTA-3717 comprising:
    a) growing a culture of *Pichia stipitis*; derived from Northern Regional Research Lab (NRRL), Agricultural Research Service, USDA, on toxic prehydrolysate of a blend of whole tree softwoods, hardwoods, agricultural residues, grain processing intermediates and residues, or mixtures or blends thereof;
    b) maximizing the number of cell generations and using all generated cells by splitting and transferring culture progeny into additional cultures while said yeast have active mitochondria by gradually increasing prehydrolysate concentration while increasing aeration and reducing nutrient concentration in an amount sufficient to obligate yeast dependency on oxygen at an oxygen absorption rate of 0.001 to $\leq 0.7$ mM of $O_2$ per liter of culture per minute;
    c) gradually substituting for yeast extract a lesser amount of corn-steep liquor;
    d) replacing a nitrogen source of peptone with a lesser amount of ammonium sulfate; and
    e) collecting cells of *Pichia stipitis* strain NPw9 having ATCC accession No. PTA3717.

11. The process of claim 10 wherein said prehydrolysate is debarked softwood Douglas Fir.

12. The process of claim 10 wherein said toxic prehydrolysate is a blend of whole tree softwoods such as White Fir and Ponderosa pine.

13. The process of claim 10 wherein said toxic prehydrolysate is a blend of mixed forest softwood and hardwood waste.

14. The process of claim 10 wherein said toxic prehydrolysate is a blend of agricultural wastes, residues, grain processing internediates or residues, or MSW, or mixtures thereof.

15. The process of claim 10 wherein said toxic prehydrolysate is a blend of hardwoods and agricultural waste.

16. The process of claim 10 wherein said toxic prehydrolysate is a blend of hardwoods, softwoods, agricultural waste and MSW.

17. The process of claim 11 wherein said toxic prehydrolysate is in the form of a slurry.

18. The process of claim 12 wherein said toxic prehydrolysate is in the form of a filtrate.

19. The process of claim 16 wherein said toxic prehydrolysate has a pH of about 7.5 to about 3, but preferably about 5.0.

20. The process of claim 6 wherein said grain processing intermediate and residues are selected from the group consisting of corn fiber, distiller's grains and stillage.

* * * * *